US012745942B2

(12) United States Patent
Sowards et al.

(10) Patent No.: US 12,745,942 B2
(45) Date of Patent: Sep. 29, 2026

(54) FIBER OPTIC ENABLED STYLET

(71) Applicant: Bard Access Systems, Inc., Salt Lake City, UT (US)

(72) Inventors: Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 547 days.

(21) Appl. No.: 18/075,280

(22) Filed: Dec. 5, 2022

(65) Prior Publication Data

US 2024/0180470 A1 Jun. 6, 2024

(51) Int. Cl.
*A61B 5/28* (2021.01)
*A61M 25/01* (2006.01)

(52) U.S. Cl.
CPC ....... *A61B 5/28* (2021.01); *A61M 2025/0166* (2013.01)

(58) Field of Classification Search
CPC ......... A61M 2025/0166; A61B 5/6852; A61B 5/6851; A61B 2034/2061; A61B 2090/306; A61B 1/00167
See application file for complete search history.

(56) References Cited

U.S. PATENT DOCUMENTS

| | | | |
|---|---|---|---|
| 3,493,288 | A | 2/1970 | Oltman et al. |
| 4,768,855 | A | 9/1988 | Nishi et al. |
| 4,777,955 | A | 10/1988 | Brayton et al. |
| 4,813,429 | A | 3/1989 | Eshel et al. |
| 4,898,176 | A | 2/1990 | Petre |
| 4,984,581 | A | 1/1991 | Stice |
| 5,099,845 | A | 3/1992 | Besz et al. |
| 5,163,935 | A | 11/1992 | Black et al. |

(Continued)

FOREIGN PATENT DOCUMENTS

| | | | |
|---|---|---|---|
| CA | 3025240 | A1 | 11/2017 |
| DE | 102016109601 | A1 | 11/2017 |

(Continued)

OTHER PUBLICATIONS

U.S. Appl. No. 17/217,852, filed Mar. 30, 2021 Restriction Requirement dated Mar. 21, 2023.

(Continued)

*Primary Examiner* — Oommen Jacob
(74) *Attorney, Agent, or Firm* — Rutan & Tucker LLP

(57) ABSTRACT

A catheter placement system that includes a catheter placement device having elongate body configured for insertion into a catheter lumen, where the elongate body includes a body lumen. A compartment at a proximal end of the body is in fluid communication with the body lumen. A saline solution disposed within the compartment and the body lumen defines an electrical path along the elongate body and an electrode at a distal end of the elongate body. A stylet extends along the elongate body, where the stylet includes a multi-core optical fiber extending along the stylet, and where the multi-core optical fiber includes a number of fiber Bragg gratings disposed along the optical fiber to enable shape sensing of the optical fiber. A system module optically and electrically coupled with the catheter placement device displays a shape of the elongate body and ECG waveform.

17 Claims, 4 Drawing Sheets

(56) References Cited

U.S. PATENT DOCUMENTS

| | | | |
|---|---|---|---|
| 5,178,153 | A | 1/1993 | Einzig |
| 5,207,672 | A | 5/1993 | Roth et al. |
| 5,211,165 | A | 5/1993 | Dumoulin et al. |
| 5,220,703 | A | 6/1993 | Kanayama et al. |
| 5,275,151 | A | 1/1994 | Shockey et al. |
| 5,295,212 | A | 3/1994 | Morton et al. |
| 5,423,321 | A | 6/1995 | Fontenot |
| 5,454,807 | A | 10/1995 | Lennox et al. |
| 5,517,997 | A | 5/1996 | Fontenot |
| 5,599,492 | A | 2/1997 | Engelson |
| 5,622,170 | A | 4/1997 | Schulz |
| 5,633,494 | A | 5/1997 | Danisch |
| 5,693,043 | A | 12/1997 | Kittrell et al. |
| 5,740,808 | A | 4/1998 | Panescu et al. |
| 5,827,313 | A | 10/1998 | Ream |
| 5,872,879 | A | 2/1999 | Hamm |
| 5,873,842 | A | 2/1999 | Brennen et al. |
| 5,879,306 | A | 3/1999 | Fontenot et al. |
| 5,906,579 | A | 5/1999 | Vander Salm et al. |
| 5,957,831 | A | 9/1999 | Adair |
| 6,035,229 | A | 3/2000 | Silverstein et al. |
| 6,069,698 | A | 5/2000 | Ozawa et al. |
| 6,081,741 | A | 6/2000 | Hollis |
| 6,178,346 | B1 | 1/2001 | Amundson et al. |
| 6,208,887 | B1 | 3/2001 | Clarke |
| 6,210,362 | B1 | 4/2001 | Ponzi |
| 6,258,118 | B1 | 7/2001 | Baum et al. |
| 6,319,227 | B1 | 11/2001 | Mansouri-Ruiz |
| 6,343,227 | B1 | 1/2002 | Crowley |
| 6,371,928 | B1 | 4/2002 | Mcfann et al. |
| 6,398,721 | B1 | 6/2002 | Nakamura et al. |
| 6,485,482 | B1 | 11/2002 | Belef |
| 6,563,105 | B2 | 5/2003 | Seibel et al. |
| 6,564,089 | B2 | 5/2003 | Izatt et al. |
| 6,593,884 | B1 | 7/2003 | Gilboa et al. |
| 6,597,941 | B2 | 7/2003 | Fontenot et al. |
| 6,619,857 | B2 | 9/2003 | Miyake |
| 6,650,923 | B1 | 11/2003 | Lesh et al. |
| 6,685,666 | B1 | 2/2004 | Fontenot |
| 6,687,010 | B1 | 2/2004 | Horii et al. |
| 6,690,966 | B1 | 2/2004 | Rava et al. |
| 6,701,181 | B2 | 3/2004 | Tang et al. |
| 6,711,426 | B2 | 3/2004 | Benaron et al. |
| 6,816,743 | B2 | 11/2004 | Moreno et al. |
| 6,892,090 | B2 | 5/2005 | Verard et al. |
| 6,895,267 | B2 | 5/2005 | Panescu et al. |
| 6,975,803 | B2 | 12/2005 | Koide et al. |
| 7,043,287 | B1 | 5/2006 | Khalil et al. |
| 7,132,645 | B2 | 11/2006 | Korn |
| 7,273,056 | B2 | 9/2007 | Wilson et al. |
| 7,344,533 | B2 | 3/2008 | Pearson et al. |
| 7,366,562 | B2 | 4/2008 | Dukesherer et al. |
| 7,366,563 | B2 | 4/2008 | Kleen et al. |
| 7,396,354 | B2 | 7/2008 | Rychnovsky et al. |
| 7,406,346 | B2 | 7/2008 | Kleen et al. |
| 7,515,265 | B2 | 4/2009 | Alfano et al. |
| 7,532,920 | B1 | 5/2009 | Ainsworth et al. |
| 7,587,236 | B2 | 9/2009 | Demos et al. |
| 7,603,166 | B2 | 10/2009 | Casscells, III et al. |
| 7,699,855 | B2 | 4/2010 | Anderson et al. |
| 7,729,735 | B1 | 6/2010 | Burchman |
| 7,757,695 | B2 | 7/2010 | Wilson et al. |
| 7,758,499 | B2 | 7/2010 | Adler |
| 7,840,253 | B2 | 11/2010 | Tremblay et al. |
| 7,992,573 | B2 | 8/2011 | Wilson et al. |
| 8,032,200 | B2 | 10/2011 | Tearney et al. |
| 8,054,469 | B2 | 11/2011 | Nakabayashi et al. |
| 8,060,187 | B2 | 11/2011 | Marshik-Geurts et al. |
| 8,073,517 | B1 | 12/2011 | Burchman |
| 8,078,261 | B2 | 12/2011 | Imam |
| 8,182,433 | B2 | 5/2012 | Leo et al. |
| 8,187,189 | B2 | 5/2012 | Jung et al. |
| 8,197,494 | B2 | 6/2012 | Jaggi et al. |
| 8,267,932 | B2 | 9/2012 | Baxter et al. |
| 8,369,932 | B2 | 2/2013 | Cinbis et al. |
| 8,388,541 | B2 | 3/2013 | Messerly et al. |
| 8,571,640 | B2 | 10/2013 | Holman |
| 8,597,315 | B2 | 12/2013 | Snow et al. |
| 8,622,935 | B1 | 1/2014 | Leo |
| 8,700,358 | B1 | 4/2014 | Parker, Jr. |
| 8,781,555 | B2 | 7/2014 | Burnside et al. |
| 8,798,721 | B2 | 8/2014 | Dib |
| 8,968,331 | B1 | 3/2015 | Sochor |
| 8,979,871 | B2 | 3/2015 | Tyc et al. |
| 9,119,551 | B2 | 9/2015 | Qi et al. |
| 9,186,046 | B2 | 11/2015 | Ramamurthy et al. |
| 9,339,206 | B2 | 5/2016 | Grunwald |
| 9,339,221 | B1 | 5/2016 | Heaton, II et al. |
| 9,345,510 | B2 | 5/2016 | Patel et al. |
| 9,360,630 | B2 | 6/2016 | Jenner et al. |
| 9,549,685 | B2 | 1/2017 | Cox et al. |
| 9,560,954 | B2 | 2/2017 | Jacobs et al. |
| 9,572,492 | B2 | 2/2017 | Simpson et al. |
| 9,622,706 | B2 | 4/2017 | Dick et al. |
| 9,645,326 | B1 | 5/2017 | Sausse et al. |
| 9,649,048 | B2 | 5/2017 | Cox et al. |
| 9,678,275 | B1 | 6/2017 | Griffin |
| 9,678,284 | B2 | 6/2017 | Coggi et al. |
| 9,737,213 | B1 | 8/2017 | Heaton, II et al. |
| 9,872,978 | B1 | 1/2018 | Zaborsky et al. |
| 10,231,643 | B2 | 3/2019 | Grunwald |
| 10,231,753 | B2 | 3/2019 | Burnside et al. |
| 10,258,240 | B1 | 4/2019 | Eberle et al. |
| 10,265,133 | B1 | 4/2019 | McClellan |
| 10,327,830 | B2 | 6/2019 | Grant et al. |
| 10,349,890 | B2 | 7/2019 | Misener et al. |
| 10,448,837 | B2 | 10/2019 | Manzke et al. |
| 10,492,876 | B2 | 12/2019 | Anastassiou et al. |
| 10,551,245 | B2 | 2/2020 | Do et al. |
| 10,568,586 | B2 | 2/2020 | Begin et al. |
| 10,603,126 | B2 | 3/2020 | Karguth et al. |
| 10,620,386 | B2 | 4/2020 | Van Der Mark et al. |
| 10,631,718 | B2 | 4/2020 | Petroff et al. |
| 10,687,891 | B2 | 6/2020 | Belhe et al. |
| 10,932,670 | B2 | 3/2021 | Smith et al. |
| 10,939,889 | B2 | 3/2021 | Flexman et al. |
| 10,992,078 | B2 | 4/2021 | Thompson et al. |
| 10,992,079 | B2 | 4/2021 | Stats et al. |
| 11,000,207 | B2 | 5/2021 | Burnside et al. |
| 11,000,265 | B1 | 5/2021 | Ryu et al. |
| 11,103,321 | B2 | 8/2021 | Braun et al. |
| 11,123,047 | B2 | 9/2021 | Jaffer et al. |
| 11,259,892 | B2 | 3/2022 | Hufford et al. |
| 11,284,916 | B2 | 3/2022 | Patel et al. |
| 11,369,342 | B2 | 6/2022 | Irisawa |
| 11,382,653 | B2 | 7/2022 | Patel et al. |
| 11,474,310 | B2 | 10/2022 | Sowards et al. |
| 11,525,670 | B2 | 12/2022 | Messerly et al. |
| 11,547,282 | B2 | 1/2023 | Weise et al. |
| 11,607,150 | B2 | 3/2023 | Schweikert et al. |
| 11,621,518 | B2 | 4/2023 | Stats et al. |
| 11,630,009 | B2 | 4/2023 | Misener et al. |
| 11,707,205 | B2 | 7/2023 | Messerly et al. |
| 11,806,096 | B2 | 11/2023 | Flatt et al. |
| 11,850,073 | B2 | 12/2023 | Wright et al. |
| 11,931,112 | B2 | 3/2024 | Thompson et al. |
| 12,038,338 | B2 | 7/2024 | Misener et al. |
| 12,048,478 | B2 | 7/2024 | Tegg et al. |
| 12,089,815 | B2 | 9/2024 | Sowards et al. |
| 2002/0019627 | A1 | 2/2002 | Maguire et al. |
| 2002/0087206 | A1 | 7/2002 | Hirschberg et al. |
| 2002/0166190 | A1 | 11/2002 | Miyake et al. |
| 2002/0188285 | A1 | 12/2002 | Brown |
| 2002/0198457 | A1 | 12/2002 | Tearney et al. |
| 2003/0045798 | A1 | 3/2003 | Hular et al. |
| 2003/0092995 | A1 | 5/2003 | Thompson |
| 2004/0039274 | A1 | 2/2004 | Benaron et al. |
| 2004/0111020 | A1 | 6/2004 | Long |
| 2004/0111147 | A1 | 6/2004 | Rabkin et al. |
| 2004/0242995 | A1 | 12/2004 | Maschke |
| 2004/0247268 | A1 | 12/2004 | Ishihara et al. |
| 2004/0260182 | A1 | 12/2004 | Zuluaga et al. |
| 2005/0033264 | A1 | 2/2005 | Redinger |
| 2005/0113719 | A1 | 5/2005 | Saadat |

(56) References Cited

U.S. PATENT DOCUMENTS

2005/0272975 A1 12/2005 McWeeney et al.
2006/0013523 A1 1/2006 Childlers et al.
2006/0030753 A1 2/2006 Boutillette et al.
2006/0036164 A1 2/2006 Wilson et al.
2006/0064058 A1 3/2006 Coyle
2006/0069305 A1 3/2006 Couvillon et al.
2006/0100610 A1 5/2006 Wallace et al.
2006/0189959 A1 8/2006 Schneiter
2006/0200049 A1 9/2006 Leo et al.
2006/0241395 A1 10/2006 Kruger et al.
2006/0241492 A1 10/2006 Boese et al.
2007/0060847 A1 3/2007 Leo et al.
2007/0156019 A1 7/2007 Larkin et al.
2007/0179485 A1 8/2007 Yeik et al.
2007/0201793 A1 8/2007 Askins et al.
2007/0225563 A1 9/2007 Ogino
2007/0253673 A1 11/2007 Nielsen et al.
2007/0265503 A1* 11/2007 Schlesinger ........... A61B 5/065 600/182
2007/0287886 A1 12/2007 Saadat
2007/0299425 A1 12/2007 Waner et al.
2008/0034519 A1 2/2008 Fujiwara
2008/0172119 A1 7/2008 Yamasaki et al.
2008/0183128 A1 7/2008 Morriss et al.
2008/0281293 A1 11/2008 Peh et al.
2008/0285909 A1 11/2008 Younge et al.
2009/0005675 A1 1/2009 Grunwald et al.
2009/0018393 A1 1/2009 Dick et al.
2009/0046980 A1 2/2009 Rohlen
2009/0062634 A1 3/2009 Say et al.
2009/0137952 A1 5/2009 Ramamurthy et al.
2009/0208143 A1 8/2009 Yoon et al.
2009/0227992 A1 9/2009 Nir et al.
2009/0234328 A1 9/2009 Cox et al.
2009/0253967 A1 10/2009 Gill et al.
2009/0270729 A1 10/2009 Corbucci et al.
2009/0304582 A1 12/2009 Rousso et al.
2009/0318757 A1 12/2009 Singh
2009/0324161 A1 12/2009 Prisco
2010/0016729 A1 1/2010 Futrell
2010/0030063 A1 2/2010 Lee et al.
2010/0063534 A1 3/2010 Kugler et al.
2010/0114115 A1 5/2010 Schlesinger et al.
2010/0114190 A1 5/2010 Bendett et al.
2010/0139669 A1 6/2010 Piferi et al.
2010/0204569 A1 8/2010 Burnside et al.
2010/0274235 A1 10/2010 Mihajlovic et al.
2010/0286531 A1 11/2010 Ryan et al.
2010/0292758 A1 11/2010 Lee et al.
2011/0087112 A1 4/2011 Leo et al.
2011/0098533 A1 4/2011 Onoda et al.
2011/0144481 A1 6/2011 Feer et al.
2011/0144630 A1 6/2011 Loeb
2011/0166442 A1 7/2011 Sarvazyan
2011/0172680 A1 7/2011 Younge et al.
2011/0178509 A1 7/2011 Zerfas et al.
2011/0196248 A1 8/2011 Grunwald
2011/0245662 A1 10/2011 Eggers et al.
2011/0295108 A1 12/2011 Cox et al.
2012/0046562 A1 2/2012 Powers et al.
2012/0116161 A1 5/2012 Nieman et al.
2012/0143029 A1 6/2012 Silverstein et al.
2012/0184827 A1 7/2012 Shwartz et al.
2012/0184955 A1 7/2012 Pivotto et al.
2012/0289779 A1 11/2012 Kinoshita et al.
2012/0321243 A1 12/2012 Younge et al.
2013/0096482 A1 4/2013 Bertrand et al.
2013/0104884 A1 5/2013 Vazales et al.
2013/0150732 A1 6/2013 Manzke et al.
2013/0188855 A1 7/2013 Desjardins et al.
2013/0190741 A1 7/2013 Moll et al.
2013/0204124 A1 8/2013 Duindam et al.
2013/0211246 A1 8/2013 Parasher
2013/0296652 A1 11/2013 Farr
2013/0296693 A1 11/2013 Wenzel et al.
2013/0310668 A1 11/2013 Young
2013/0324840 A1 12/2013 Zhongping et al.
2014/0031674 A1 1/2014 Newman et al.
2014/0046261 A1 2/2014 Newman et al.
2014/0058368 A1 2/2014 Hogue
2014/0073950 A1 3/2014 Akui et al.
2014/0088413 A1 3/2014 Von Bucsh et al.
2014/0121468 A1 5/2014 Eichenholz
2014/0155948 A1 6/2014 Walsh et al.
2014/0180087 A1 6/2014 Millett et al.
2014/0188133 A1 7/2014 Misener
2014/0221829 A1 8/2014 Maitland et al.
2014/0259477 A1 9/2014 Huang
2014/0268167 A1 9/2014 Friedman et al.
2014/0275997 A1 9/2014 Chopra et al.
2014/0318825 A1 10/2014 Erb et al.
2014/0323887 A1* 10/2014 Anderson .............. A61B 5/026 600/505
2014/0378945 A1 12/2014 Beri
2015/0029511 A1 1/2015 Hooft et al.
2015/0031987 A1 1/2015 Pameijer et al.
2015/0045649 A1 2/2015 O'Dea et al.
2015/0080688 A1 3/2015 Cinbis et al.
2015/0099979 A1 4/2015 Caves et al.
2015/0105654 A1 4/2015 Meyer
2015/0119700 A1 4/2015 Liang et al.
2015/0119724 A1 4/2015 Weber et al.
2015/0209113 A1 7/2015 Burkholz et al.
2015/0209117 A1 7/2015 Flexman et al.
2015/0244465 A1 8/2015 Chou et al.
2015/0270900 A1 9/2015 Hilario et al.
2015/0272445 A1 10/2015 Rozental et al.
2015/0301288 A1 10/2015 Thornton, Jr.
2015/0305816 A1 10/2015 Hadzic
2015/0320977 A1 11/2015 Vitullo et al.
2016/0018602 A1 1/2016 Govari et al.
2016/0151115 A1 6/2016 Karguth et al.
2016/0166326 A1 6/2016 Bakker et al.
2016/0166341 A1 6/2016 Ordachita et al.
2016/0184020 A1 6/2016 Kowalewski et al.
2016/0256228 A1 9/2016 Haartsen et al.
2016/0262627 A1 9/2016 Hecker et al.
2016/0302762 A1 10/2016 Stigall et al.
2016/0331360 A1 11/2016 Hera et al.
2016/0354038 A1 12/2016 Demirtas et al.
2016/0357007 A1 12/2016 Swanson
2016/0374589 A1 12/2016 Misener et al.
2017/0017048 A1 1/2017 Coggi et al.
2017/0020394 A1 1/2017 Harrington
2017/0052091 A1 2/2017 Mori
2017/0079548 A1 3/2017 Silverstein et al.
2017/0082806 A1 3/2017 Van Der Mark et al.
2017/0196479 A1 7/2017 Liu et al.
2017/0201036 A1 7/2017 Cohen et al.
2017/0215973 A1 8/2017 Flexman et al.
2017/0231699 A1 8/2017 Flexman et al.
2017/0273542 A1 9/2017 Au
2017/0273565 A1 9/2017 Ma et al.
2017/0273628 A1 9/2017 Ofek et al.
2017/0290542 A1 10/2017 Chandrasoma
2017/0296037 A1 10/2017 Yoshino
2017/0303824 A1 10/2017 Schlesinger et al.
2017/0311924 A1 11/2017 Sudol
2017/0333136 A1 11/2017 Hladio et al.
2017/0348063 A1 12/2017 Braun et al.
2018/0067268 A1 3/2018 Murakami et al.
2018/0093078 A1 4/2018 Patil et al.
2018/0095231 A1 4/2018 Lowell et al.
2018/0113038 A1 4/2018 Janabi-Sharifi et al.
2018/0116551 A1 5/2018 Newman et al.
2018/0140170 A1 5/2018 Van Putten et al.
2018/0175547 A1 6/2018 Hsu
2018/0239124 A1 8/2018 Naruse et al.
2018/0250088 A1 9/2018 Brennan et al.
2018/0264227 A1 9/2018 Flexman et al.
2018/0289243 A1 10/2018 Landey et al.
2018/0289390 A1 10/2018 Amorizzo et al.
2018/0289927 A1 10/2018 Messerly
2018/0317751 A1 11/2018 Kuboi et al.

(56) References Cited

U.S. PATENT DOCUMENTS

| | | | |
|---|---|---|---|
| 2018/0339134 | A1 | 11/2018 | Leo |
| 2018/0360545 | A1 | 12/2018 | Cole et al. |
| 2018/0369432 | A1 | 12/2018 | Zaborsky |
| 2019/0008376 | A1 | 1/2019 | Wortelboer et al. |
| 2019/0059743 | A1 | 2/2019 | Ramachandran et al. |
| 2019/0110838 | A1 | 4/2019 | Martinez et al. |
| 2019/0110839 | A1 | 4/2019 | Rafii-Tari et al. |
| 2019/0110844 | A1 | 4/2019 | Misener et al. |
| 2019/0142528 | A1 | 5/2019 | Vertikov |
| 2019/0192818 | A1 | 6/2019 | Koda et al. |
| 2019/0212761 | A1 | 7/2019 | Swanson et al. |
| 2019/0223706 | A1 | 7/2019 | Takeuchi et al. |
| 2019/0235182 | A1 | 8/2019 | Cheng |
| 2019/0237902 | A1 | 8/2019 | Thompson et al. |
| 2019/0271815 | A1 | 9/2019 | Van Der Mark et al. |
| 2019/0321110 | A1 | 10/2019 | Grunwald et al. |
| 2019/0343424 | A1 | 11/2019 | Blumenkranz et al. |
| 2019/0357875 | A1 | 11/2019 | Ql et al. |
| 2019/0374196 | A1 | 12/2019 | Courtney et al. |
| 2020/0022587 | A1 | 1/2020 | Glover et al. |
| 2020/0046434 | A1 | 2/2020 | Graetzel et al. |
| 2020/0060718 | A1 | 2/2020 | Patel et al. |
| 2020/0069192 | A1 | 3/2020 | Sanborn et al. |
| 2020/0093353 | A1 | 3/2020 | Tezuka et al. |
| 2020/0155073 | A1 | 5/2020 | Hwang et al. |
| 2020/0170724 | A1 | 6/2020 | Flatt et al. |
| 2020/0188036 | A1 | 6/2020 | Ding et al. |
| 2020/0238051 | A1 | 7/2020 | Hwang et al. |
| 2020/0261720 | A1 | 8/2020 | Danitz et al. |
| 2020/0275827 | A1 | 9/2020 | Weise et al. |
| 2020/0305983 | A1 | 10/2020 | Yampolsky et al. |
| 2021/0007796 | A1 | 1/2021 | Panescu et al. |
| 2021/0030504 | A1 | 2/2021 | Thompson et al. |
| 2021/0045814 | A1 | 2/2021 | Thompson et al. |
| 2021/0113274 | A1 | 4/2021 | Bydlon et al. |
| 2021/0154440 | A1 | 5/2021 | Misener |
| 2021/0156676 | A1* | 5/2021 | Messerly ............... G01B 11/24 |
| 2021/0205585 | A1 | 7/2021 | Ullmann et al. |
| 2021/0215871 | A1 | 7/2021 | Hayes et al. |
| 2021/0268229 | A1 | 9/2021 | Sowards et al. |
| 2021/0271035 | A1 | 9/2021 | Sowards et al. |
| 2021/0275256 | A1 | 9/2021 | Sowards et al. |
| 2021/0275257 | A1 | 9/2021 | Prior et al. |
| 2021/0278604 | A1 | 9/2021 | Rohr Daniel et al. |
| 2021/0282867 | A1 | 9/2021 | Tegg et al. |
| 2021/0290315 | A1 | 9/2021 | Lampert et al. |
| 2021/0298680 | A1 | 9/2021 | Sowards et al. |
| 2021/0299879 | A1 | 9/2021 | Pinter et al. |
| 2021/0325172 | A1 | 10/2021 | Hendriks et al. |
| 2021/0330398 | A1 | 10/2021 | Tegg et al. |
| 2021/0389519 | A1 | 12/2021 | Choi et al. |
| 2021/0401456 | A1 | 12/2021 | Cox et al. |
| 2021/0401509 | A1 | 12/2021 | Misener et al. |
| 2021/0402144 | A1 | 12/2021 | Messerly |
| 2022/0034733 | A1 | 2/2022 | Misener et al. |
| 2022/0039632 | A1 | 2/2022 | Polejaev et al. |
| 2022/0039744 | A1 | 2/2022 | Koenig |
| 2022/0110695 | A1 | 4/2022 | Sowards et al. |
| 2022/0110706 | A1 | 4/2022 | Misener et al. |
| 2022/0133401 | A1 | 5/2022 | O'Brien et al. |
| 2022/0152349 | A1 | 5/2022 | Sowards et al. |
| 2022/0160209 | A1 | 5/2022 | Sowards et al. |
| 2022/0188285 | A1 | 6/2022 | Ofenloch |
| 2022/0257975 | A1 | 8/2022 | Croll et al. |
| 2022/0330891 | A1 | 10/2022 | Sowards et al. |
| 2022/0361762 | A1 | 11/2022 | Lalancette et al. |
| 2023/0082991 | A1 | 3/2023 | Sowards et al. |
| 2023/0149080 | A1 | 5/2023 | Wong et al. |
| 2023/0285085 | A1 | 9/2023 | Misener et al. |
| 2023/0292997 | A1 | 9/2023 | Sowards et al. |
| 2023/0293243 | A1 | 9/2023 | Sowards et al. |
| 2023/0320663 | A1 | 10/2023 | Misener et al. |
| 2023/0338090 | A1 | 10/2023 | Misener et al. |
| 2023/0346314 | A1 | 11/2023 | Sowards et al. |
| 2023/0346482 | A1 | 11/2023 | Sowards et al. |
| 2023/0379057 | A1 | 11/2023 | Moore |
| 2023/0414293 | A1 | 12/2023 | Farley et al. |
| 2023/0417998 | A1 | 12/2023 | Misener et al. |
| 2024/0016425 | A1 | 1/2024 | Sowards et al. |
| 2024/0094475 | A1 | 3/2024 | Misener et al. |
| 2024/0180470 | A1* | 6/2024 | Sowards .............. A61B 5/6851 |
| 2024/0215917 | A1 | 7/2024 | Sowards et al. |
| 2024/0423456 | A1 | 12/2024 | Sowards et al. |
| 2025/0176853 | A1 | 6/2025 | Sowards et al. |
| 2025/0186134 | A1 | 6/2025 | Sowards et al. |
| 2025/0249208 | A1 | 8/2025 | Sowards et al. |
| 2025/0288366 | A1 | 9/2025 | Misener et al. |
| 2026/0076763 | A1 | 3/2026 | Sowards et al. |

FOREIGN PATENT DOCUMENTS

| | | | |
|---|---|---|---|
| EP | 2240111 | A2 | 10/2010 |
| EP | 2385802 | B1 | 8/2013 |
| EP | 2417484 | B1 | 12/2014 |
| EP | 3266383 | A1 | 1/2018 |
| EP | 2809249 | B1 | 12/2018 |
| EP | 3545849 | A1 | 10/2019 |
| EP | 3725252 | A1 | 10/2020 |
| NO | 2022109045 | A1 | 5/2022 |
| WO | 99/64099 | A1 | 12/1999 |
| WO | 2006080076 | A1 | 8/2006 |
| WO | 2006122001 | A2 | 11/2006 |
| WO | 2009155325 | A2 | 12/2009 |
| WO | 2011141830 | A1 | 11/2011 |
| WO | 2011150376 | A1 | 12/2011 |
| WO | 2012064769 | A2 | 5/2012 |
| WO | 2012135339 | A1 | 10/2012 |
| WO | 2013114376 | A1 | 8/2013 |
| WO | 2014049555 | A1 | 4/2014 |
| WO | 2015055413 | A1 | 4/2015 |
| WO | 2015074045 | A2 | 5/2015 |
| WO | 2016061431 | A1 | 4/2016 |
| WO | 2016193051 | A1 | 12/2016 |
| WO | 2018071490 | A1 | 4/2018 |
| WO | 2018/096491 | A1 | 5/2018 |
| WO | 2018187708 | A1 | 10/2018 |
| WO | 2019037071 | A1 | 2/2019 |
| WO | 2019046769 | A1 | 3/2019 |
| WO | 2019230713 | A1 | 12/2019 |
| WO | 2020142470 | A1 | 7/2020 |
| WO | 2021021408 | A1 | 2/2021 |
| WO | 2021030092 | A1 | 2/2021 |
| WO | 2021108688 | A1 | 6/2021 |
| WO | 2021108697 | A1 | 6/2021 |
| WO | 2021144317 | A1 | 7/2021 |
| WO | 2021178578 | A1 | 9/2021 |
| WO | 2022031613 | A1 | 2/2022 |
| WO | 2022081586 | A1 | 4/2022 |
| WO | 2022081723 | A1 | 4/2022 |
| WO | 2022115624 | A1 | 6/2022 |
| WO | 2022221608 | A1 | 10/2022 |
| WO | 2023043947 | A1 | 3/2023 |
| WO | 2023172652 | A1 | 9/2023 |
| WO | 2023177822 | A1 | 9/2023 |
| WO | 2023177889 | A1 | 9/2023 |
| WO | 2023200734 | A1 | 10/2023 |
| WO | 2023205257 | A1 | 10/2023 |
| WO | 2023212096 | A1 | 11/2023 |
| WO | 2023212098 | A1 | 11/2023 |
| WO | 2023249952 | A1 | 12/2023 |
| WO | 2024015464 | A1 | 1/2024 |
| WO | 2024123837 | A1 | 6/2024 |

OTHER PUBLICATIONS

PCT/US2021 /059755 filed Nov. 17, 2021 International Search Report and Written Opinion dated Apr. 29, 2022.

PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.

PCT/US2021/020732 filed Mar. 3, 2021 International Search Report and Written Opinion dated Jul. 5, 2021.

(56) References Cited

OTHER PUBLICATIONS

PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
PCT/US2021/060849 filed Nov. 24, 2021 International Search Report and Written Opinion dated Mar. 9, 2022.
PCT/US2022/043698 filed Sep. 15, 2022 International Search Report and Written Opinion dated Dec. 19. 2022.
U.S. Appl. No. 17/967,794, filed Oct. 17, 2022 Notice of Allowance dated Feb. 15, 2023.
U.S. Appl. No. 17/185,777, filed Feb. 25, 2021 Non-Final Office Action dated Feb. 9, 2022.
U.S. Appl. No. 17/185,777, filed Feb. 25, 2021 Notice of Allowance dated Jun. 10, 2022.
PCT/US2023/015536 filed Mar. 17, 2023 International Preliminary Report on Patentability dated Sep. 10, 2024.
PCT/US2023/018076 filed Apr. 10, 2023 International Preliminary Report on Patentability dated Oct. 8, 2024.
PCT/US2023/019130 filed Apr. 19, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Notice of Allowance dated Nov. 8, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Notice of Allowance dated Oct. 23, 2024.
U.S. Appl. No. 17/689,773, filed Mar. 8, 2022 Advisory Action dated Nov. 1, 2024.
U.S. Appl. No. 17/696,675, filed Mar. 16, 2022 Final Office Action dated Dec. 5, 2024.
U.S. Appl. No. 17/725,394, filed Apr. 20, 2022 Non-Final Office Action dated Nov. 19, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Advisory Action dated Oct. 24, 2024.
U.S. Appl. No. 17/849,447, filed Jun. 24, 2022 Restriction Requirement dated Apr. 15, 2024.
U.S. Appl. No. 17/863,211, filed Jul. 12, 2022 Restriction Requirement dated Nov. 15, 2024.
U.S. Appl. No. 18/141,289, filed Apr. 28, 2023 Non-Final Office Action dated Sep. 28, 2024.
U.S. Appl. No. 18/524,620, filed Nov. 30, 2023 Notice of Allowance dated Sep. 12, 2024.
U.S. Appl. No. 17/187,536, filed Feb. 26, 2021 Final Office Action dated Jul. 2, 2024.
U.S. Appl. No. 17/191,551, filed Mar. 3, 2021 Non-Final Office Action dated Aug. 16, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/696,675, filed Mar. 16, 2022 Non-Final Office Action dated Jun. 11, 2024.
U.S. Appl. No. 17/725,394, filed Apr. 20, 2022 Non-Final Office Action dated Jun. 17, 2024.
U.S. Appl. No. 17/849,447, filed Jun. 24, 2022 Final Office Action dated Aug. 8, 2024.
U.S. Appl. No. 18/524,620, filed Nov. 30, 2023 Non-Final Office Action dated Jun. 18, 2024.
U.S. Appl. No. 17/689,773, filed Mar. 8, 2022 Notice of Allowance dated Jan. 15, 2025.
U.S. Appl. No. 17/696,675, filed Mar. 16, 2022 Advisory Action dated Feb. 6, 2025.
U.S. Appl. No. 17/731,129, filed Apr. 27, 2022 Restriction Requirement dated Feb. 28, 2025.
U.S. Appl. No. 17/731,155, filed Apr. 27, 2022 Final Office Action dated Jan. 24, 2025.
U.S. Appl. No. 17/849,447, filed Jun. 24, 2022 Non-Final Office Action dated Jan. 17, 2025.
U.S. Appl. No. 17/863,211, filed Jul. 12, 2022 Non-Final Office Action dated Jan. 29, 2025.
U.S. Appl. No. 17/945,875, filed Sep. 15, 2022 Non-Final Office Action dated Feb. 27, 2025.
U.S. Appl. No. 18/141,289, filed Apr. 28, 2023 Notice of Allowance dated Jan. 10, 2025.
U.S. Appl. No. 18/607,165 filed Mar. 15, 2024 Non-Final Office Action dated Jan. 15, 2025.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020042 filed Apr. 26, 2023 International Search Report and Written Opinion dated Sep. 26, 2023.
PCT/US2023/020044 filed Apr. 26, 2023 International Search Report and Written Opinion dated Jul. 19, 2023.
PCT/US2023/025757 filed Jun. 20, 2023 International Search Report and Written Opinion dated Sep. 11, 2023.
U.S. Appl. No. 17/187,536, filed Feb. 26, 2021 Final Office Action dated Sep. 20, 2023.
U.S. Appl. No. 17/217,852, filed Mar. 30, 2021 Ex Parte Quayle Action dated Sep. 8, 2023.
U.S. Appl. No. 17/499,644, filed Oct. 12, 2021 Notice of Allowance dated Sep. 18, 2023.
U.S. Appl. No. 17/499,644, filed Oct. 12, 2021 Restriction Requirement dated Jul. 11, 2023.
U.S. Appl. No. 17/697,895, filed Mar. 17, 2022 Advisory Action dated Sep. 8, 2023.
U.S. Appl. No. 17/697,895, filed Mar. 17, 2022 Final Office Action dated Aug. 16, 2023.
U.S. Appl. No. 17/529,022, filed Nov. 17, 2021 Notice of Allowance dated Jan. 2, 2025.
U.S. Appl. No. 17/529,022, filed Nov. 17, 2021 Restriction Requirement dated May 2, 2024.
U.S. Appl. No. 17/717,919, filed Apr. 11, 2022 Restriction Requirement dated Apr. 23, 2025.
U.S. Appl. No. 17/721,333, filed Apr. 14, 2022 Restriction Requirement dated May 6, 2025.
U.S. Appl. No. 17/725,394, filed Apr. 20, 2022 Final Office Action dated Mar. 27, 2025.
U.S. Appl. No. 17/731,129, filed Apr. 27, 2022 Non-Final Office Action dated Apr. 28, 2025.
U.S. Appl. No. 17/731,155, filed Apr. 27, 2022 Advisory Action dated Apr. 3, 2025.
U.S. Appl. No. 17/849,447, filed Jun. 24, 2022 Final Office Action dated May 7, 2025.
U.S. Appl. No. 18/607,165, filed Mar. 15, 2024 Notice of Allowance dated Apr. 3, 2025.
PCT/US2022/024934 filed Apr. 14, 2022 International Search Report and Written Opinion dated Jul. 18. 2022.
PCT/US2023/027527 filed Jul. 12, 2023 International Search Report and Written Opinion dated Oct. 16, 2023.
U.S. Appl. No. 17/187,536, filed Feb. 26, 2021 Advisory Action dated Nov. 21, 2023.
U.S. Appl. No. 17/187,536, filed Feb. 26, 2021 Non-Final Office Action dated Dec. 15, 2023.
U.S. Appl. No. 17/217,852, filed Mar. 30, 2021 Notice of Allowance dated Nov. 7, 2023.
U.S. Appl. No. 17/535,406, filed Nov. 24, 2021 Restriction Requirement dated Nov. 24, 2023.
U.S. Appl. No. 17/697,895, filed Mar. 17, 2022 Non-Final Office Action dated Jan. 11, 2024.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array

(56) References Cited

OTHER PUBLICATIONS inscribed in polyimide-coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/535,406, filed Nov. 24, 2021 Non-Final Office Action dated Feb. 15, 2024.
U.S. Appl. No. 17/689,773, filed Mar. 8, 2022 Non-Final Office Action dated Mar. 19, 2024.
U.S. Appl. No. 17/697,895, filed Mar. 17, 2022 Notice of Allowance dated May 8, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
U.S. Appl. No. 17/187,536, filed Feb. 26, 2021 Non-Final Office Action dated May 17, 2023.
U.S. Appl. No. 17/217,852, filed Mar. 30, 2021 Non Final Office Action dated Jun. 7, 2023.
U.S. Appl. No. 17/697,895, filed Mar. 17, 2022 Non Final Office Action dated Jun. 14, 2023.
U.S. Appl. No. 17/696,675, filed Mar. 16, 2022 Notice of Allowance dated Jun. 17, 2025.
U.S. Appl. No. 17/717,919, filed Apr. 11, 2022 Non-Final Office Action dated Jul. 1, 2025.
U.S. Appl. No. 17/725,394, filed Apr. 20, 2022 Advisory Action dated Jun. 5, 2025.
U.S. Appl. No. 17/725,394, filed Apr. 20, 2022 Non-Final Office Action dated Jun. 25, 2025.
U.S. Appl. No. 17/731,129, filed Apr. 27, 2022 Final Office Action dated Aug. 27, 2025.
U.S. Appl. No. 17/731,155, filed Apr. 27, 2022 Non-Final Office Action dated Jul. 15, 2025.
U.S. Appl. No. 17/849,447, filed Jun. 24, 2022 Ex Parte Quayle Action dated Sep. 4, 2025.
U.S. Appl. No. 17/863,211, filed Jul. 12, 2022 Final Office Action dated Jun. 3, 2025.
U.S. Appl. No. 17/945,875, filed Sep. 15, 2022 Notice of Allowance dated Jul. 21, 2025.
U.S. Appl. No. 17/717,919, filed Apr. 11, 2022 Notice of Allowance dated Dec. 3, 2025.
U.S. Appl. No. 17/721,333, filed Apr. 14, 2022 Non-Final Office Action dated Oct. 16, 2025.
U.S. Appl. No. 17/725,394, filed Apr. 20, 2022 Final Office Action dated Nov. 19, 2025.
U.S. Appl. No. 17/731,129, filed Apr. 27, 2022 Advisory Action dated Oct. 30, 2025.
U.S. Appl. No. 17/849,447, filed Jun. 24, 2022 Notice of Allowance dated Nov. 19, 2025.
U.S. Appl. No. 17/863,211, filed Jul. 12, 2022 Advisory Action dated Sep. 11, 2025.
U.S. Appl. No. 17/863,211, filed Jul. 12, 2022 Notice of Allowance dated Oct. 22, 2025.
PCT/US2025/056170 filed Nov. 19, 2025 International Search Report and Written Opinion dated Apr. 23, 2026.
U.S. Appl. No. 17/721,333, filed Apr. 14, 2022 Notice of Allowance dated Feb. 24, 2026.
U.S. Appl. No. 17/731,129, filed Apr. 27, 2022 Notice of Allowance dated Mar. 24, 2026.
U.S. Appl. No. 17/731,155, filed Apr. 27, 2022 Final Office Action dated Feb. 9, 2026.
U.S. Appl. No. 18/827,243, filed Sep. 6, 2024 Non-Final Office Action dated Apr. 15, 2026.
U.S. Appl. No. 19/049,986, filed Feb. 10, 2025 Restriction Requirement dated Apr. 22, 2026.
U.S. Appl. No. 19/188,439, filed Apr. 24, 2025 Restriction Requirement dated Apr. 10, 2026.

* cited by examiner 125
131
124
130

100
50
51
52
110
111
115
116
145
137
135
120
125A
125B
142
130B
140
125
124
136
130
135
130D
141
126
127
155
146
126A
128
128A
130C
130A
150

FIBER OPTIC ENABLED STYLET

BACKGROUND

In the past, certain intravascular guidance of medical devices, such as guidewires and catheters for example, have used fluoroscopic methods for tracking tips of the medical devices and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

More recently, electromagnetic tracking systems have been used involving stylets. Generally, electromagnetic tracking systems feature three components: a field generator, a sensor unit and control unit. The field generator uses several coils to generate a position—varying magnetic field, which is used to establish a coordinate space. Attached to the stylet, such as near a distal end (tip) of the stylet for example, the sensor unit includes small coils in which current is induced via the magnetic field. Based on the electrical properties of each coil, the position and orientation of the medical device may be determined within the coordinate space. The control unit controls the field generator and captures data from the sensor unit.

Although electromagnetic tracking systems avoid line-of-sight reliance in tracking the tip of a stylet while obviating radiation exposure and potentially harmful contrast media associated with fluoroscopic methods, electromagnetic tracking systems are prone to interference. More specifically, since electromagnetic tracking systems depend on the measurement of magnetic fields produced by the field generator, these systems are subject to electromagnetic field interference, which may be caused by the presence of many different types of consumer electronics such as cellular telephones. Additionally, electromagnetic tracking systems are subject to signal drop out, depend on an external sensor, and are defined to a limited depth range. U.S. Pub. No. 2022/0034733 titled BRAGG GRATED FIBER OPTIC FLUCTUATION SENSING AND MONITORING SYSTEM, showing and describing a fiber optic shape sensing system and method, is incorporated by reference in its entirety into this application.

Disclosed herein is a catheter placement system utilizing fiber optic shape sensing and electrical signal monitoring to assist in placement of the catheter and specific placement of the tip placement of the catheter.

SUMMARY

Disclosed herein is a catheter placement system that, according to some embodiments, includes a catheter placement device. The catheter placement device includes an elongate body configured for insertion into a catheter lumen, where the elongate body includes a body lumen extending between a body proximal end and a body distal end. The catheter placement device further includes a compartment coupled with the elongate body at the body proximal end, where the compartment is in fluid communication with the body lumen. A saline solution is disposed within the compartment and the body lumen. A stylet extends along the elongate body, and the stylet includes a multi-core optical fiber extending along the stylet, where the multi-core optical fiber includes a number of fiber Bragg gratings disposed along a length of the multi-core optical fiber.

In some embodiments, the catheter placement device is optically coupled with a system module.

In some embodiments, a distal portion of the stylet is disposed within the body lumen.

In some embodiments, the stylet includes an elongate opening extending along the distal portion, where the opening defines additional cross-sectional area of the body lumen.

In some embodiments, the system module is configured to determine a shape of the stylet based on reflected light signals emanating the fiber Bragg gratings.

In some embodiments, the system module is further configured to display an image acquired by the optical fiber.

In some embodiments, the system module is further configured to determine, based on reflected light signals emanating the fiber Bragg gratings, one or more of a temperature of the optical fiber, a motion of the optical fiber, or a displacement of fluid adjacent the optical fiber.

In some embodiments, the saline solution is electrically coupled with the system module.

In some embodiments, the stylet extends through the compartment, and a proximal portion of the stylet extends proximally away from the compartment.

In some embodiments, the proximal portion of the stylet is (i) electrically conductive, (ii) electrically coupled with the saline within the compartment, and (iii) electrically coupled with the system module.

In some embodiments, the saline solution is electrically coupled with the system module via a wire and in some embodiments, the wire extends through a sterile barrier from a sterile environment to a non-sterile environment.

In some embodiments, the catheter placement device further includes a fluid delivery device containing the saline solution, where the fluid delivery device is fluidly coupled with the compartment. In some embodiments, the compartment includes a side port, and the fluid delivery device is fluidly coupled with the compartment via the side port.

In some embodiments, the system module is configured to display an electrocardiogram waveform. In some embodiments, the system module is configured to determine a placement location of the body distal end within a patient based on the electrocardiogram waveform.

Also disclosed herein is a method that, according some embodiments, includes inserting an elongate body of a catheter placement device within a lumen of the central catheter, where the catheter placement device includes (i) a body lumen extending along the elongate body; (ii) a compartment coupled with the elongate body at a proximal end of the elongate body, where the compartment is in fluid communication with the body lumen; (iii) a saline solution disposed within the compartment and the body lumen, where the saline solution defines an electrical path along the elongate body; and (iv) a stylet extending along the elongate body, where the stylet includes a multi-core optical fiber extending along the stylet, and where the multi-core optical fiber includes a number of fiber Bragg gratings disposed along a length of the multi-core optical fiber. In such embodiments, the catheter placement device is optically and electrically coupled with a catheter placement system module. The method further includes (i) advancing the central catheter along a vasculature of the patient; (ii) determining a position of the central catheter within the patient vasculature based on a shape of the multi-core optical fiber, where the shape is determined by light reflection signals emanating from the fiber Bragg gratings; and (iv) determining a position of a distal end of the elongate body within a superior vena cava of the vasculature based on an electrocardiogram signal obtained from the patient via an electrode at the distal end.

In some embodiments of the method, the saline solution within the body lumen adjacent the distal end defines the electrode.

In some embodiments of the method, the stylet is disposed with the body lumen.

In some embodiments of the method, a syringe containing the saline solution is fluidly coupled with the compartment.

In some embodiments of the method, the saline is electrically coupled with the catheter placement system module via a wire, and the wire extends through a sterile barrier between a sterile environment and a non-sterile environment.

These and other features of the concepts provided herein will become more apparent to those of skill in the art in view of the accompanying drawings and following description, which describe particular embodiments of such concepts in greater detail.

DRAWINGS

DESCRIPTION

Figures 1, 2:
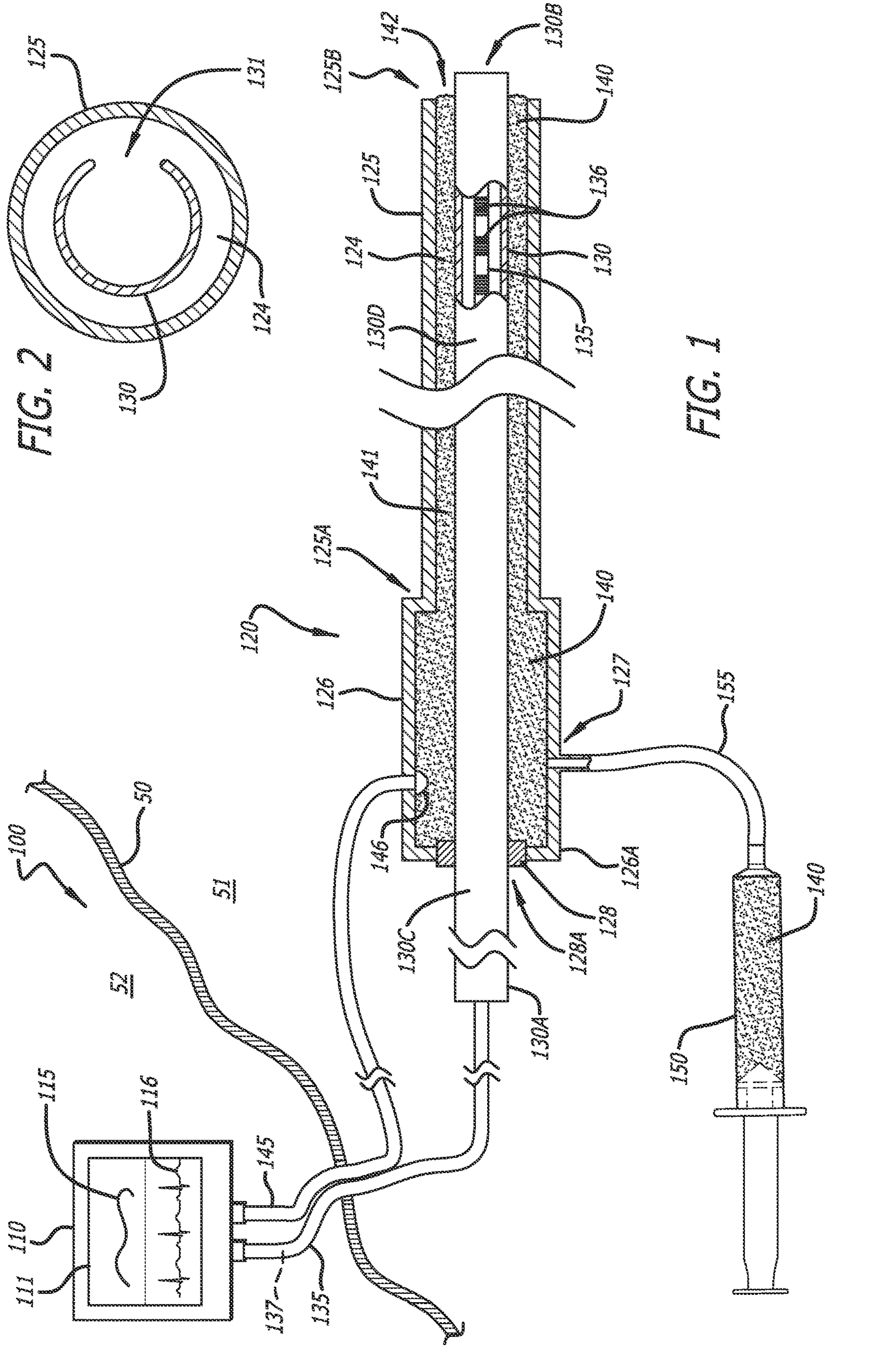
FIG. 1 illustrates a catheter placement system, in accordance with some embodiments.
FIG. 2 illustrates an end view of a catheter placement device of the system of FIG. 1, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The phrases "connected to," "coupled with," and "in communication with" refer to any form of interaction between two or more entities, including but not limited to mechanical, electrical, magnetic, electromagnetic, fluid, and thermal interaction. Two components may be coupled with each other even though they are not in direct contact with each other. For example, two components may be coupled with each other through an intermediate component.

The terms "proximal" and "distal" refer to opposite ends of a medical device, including the devices disclosed herein. As used herein, the proximal portion of a catheter placement device is the portion nearest a practitioner during use, while the distal portion is the portion at the opposite end. For example, the distal end of catheter placement device is defined as the end closest to the patient during utilization of the catheter placement device. The proximal end is the end opposite the distal end.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Unless defined otherwise, all technical and scientific terms used herein have the same meaning as commonly understood by those of ordinary skill in the art. References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

FIG. 1 illustrates a catheter placement system generally configured to assist a clinician during the placement of a catheter within a vasculature of a patient. More specifically the catheter placement system (system) 100 may (i) assist the clinician during advancement of the catheter along the vasculature and (ii) assist the clinician during placement of the distal tip of the catheter with the vasculature, such as within the superior vena cava, for example. The system 100 generally includes a catheter placement device 120 coupled with a system module 110 including a display 111.

In some instances, the system 100 may be deployed in conjunction with a sterile environment. As such, portions of the system 100 (e.g., the catheter placement device 120) may be deployed within a sterile environment 51 while other portions (e.g., the system module 110) may be deployed within a non-sterile environment 52, i.e., outside the sterile environment 51. In some instances, a sterile barrier 50 may divide the sterile environment 51 from the non-sterile environment 52. In some instances, the sterile barrier 50 may include a fabric panel, such as a drape, for example, and a number of components of the system 100 may extend through the sterile barrier 50.

The catheter placement device 120 includes an elongate body 125 that is configured for placement within a catheter lumen, such as a lumen of a central catheter, e.g., a central venous catheter (CVC) or a peripherally inserted center catheter (PICC), for example. The elongate body 125 may have sufficient length to extend between the distal tip of the catheter and an extension leg hub of the catheter. In other words, during use, a body proximal end 125A may be disposed proximal of the extension leg hub of the catheter while a body distal end 125B is disposed adjacent the distal tip of the catheter. The elongate body 125 includes a body lumen 124 extending along a length of the elongate body 125.

The catheter placement device 120 further includes a compartment 126 coupled with the elongate body at the body proximal end 125A, so that the compartment 126 is in fluid communication with the body lumen 124. A saline solution 140 is disposed within the compartment 126 and the body lumen 124. The saline solution 140 within the body lumen 124 defines an electrical path 141 extending between the body distal end 125B and the compartment 126. The body lumen 124 is open at the body distal end 125B so that the saline solution 140 may directly and electrically contact the patient. More specifically, the saline solution 140 adjacent the body distal end 125B defines a saline electrode 142, where the saline electrode 152 is configured to an acquire an electrical signal, e.g., an electrocardiogram signal, from the patient.

The catheter placement device 120 includes a fluid delivery device 150, such as a syringe, for example. The fluid delivery device 150 contains the saline solution 140. The fluid delivery device 150 is fluidly coupled with the compartment 126. In some embodiments, the fluid delivery device 150 may be coupled with the compartment 126 via a tube 155 coupled with a side port 127 of the compartment 126. During use, the fluid delivery device 150 may be provided having the saline solution 140 therein. The fluid delivery device 150 may then be coupled with the compartment 126 and the fluid delivery device 150 may dispense the saline solution 140 into the compartment 126 and along the body lumen 124.

The catheter placement device 120 further includes stylet 130 that extends along the elongate body 125. In the illustrated embodiment, the stylet 130 is disposed within the body lumen 124. However, in other embodiments, the stylet 130 may extend along an exterior of the elongate body 125 and the stylet 130 may be disposed a different lumen (not shown). The stylet 130 defines (i) a proximal portion 130C extending between a stylet proximal end 130A and the compartment 126 and (ii) a distal portion 130D extending between the compartment 126 and the stylet distal end 130B. In some embodiments, the stylet distal end 130B may be disposed adjacent the body distal end 125B. In the illustrated embodiment, the stylet 130 is generally not electrically conductive. As such, the stylet 130 may be formed a non-conductive polymeric material. In some embodiments, the distal portion 130D may include a greater stiffness than the proximal portion 130C. As the distal portion 130 is disposed along the elongate body 125 and the catheter, the greater stiffness of the distal portion 130D may assist the clinician during advancement of the catheter along the vasculature. As the proximal portion 130C is generally disposed outside the elongate body 125, the greater flexibility may allow the clinician to manipulate the catheter more easily during advancement.

The stylet 130 extends through an end wall 126A of the compartment 126. In the illustrated embodiment, the compartment 126 includes a coupling member 128 configured to sealably couple the stylet 130 to the compartment 126. The coupling member 128 includes an opening 128A through which the stylet 130 is disposed. In some embodiments, the coupling member 128 may couple the stylet 130 to the compartment 126 such that longitudinal displacement of the stylet 130 with respect to the compartment 126, including the elongate body 125, is prevented. In other embodiments, the coupling member 128 may couple the stylet 130 to the compartment 126 such that slidable displacement of the stylet 130 with respect to the compartment 126 is allowed. In some embodiments, the coupling member 128 may include an elastomeric septum and the opening 128A may be a slit extending through the septum.

In the illustrated embodiment, the catheter placement device 120 includes a wire 145 extending between the compartment 126 and the system module 110. A wire electrode 146 electrically couples the wire 145 to the saline solution 140 within the compartment 126. By way of summary, during use, the anatomy of the patient adjacent the body distal end 125B is electrically coupled with the system module 110 via the saline electrode 142, the saline solution 140 along the body lumen 124, the saline solution 140 within the compartment 126, the wire electrode 146, and the wire 145. In some instances, the wire 145 may extend through the sterile barrier 50.

The stylet includes an optical fiber 135 extending along the stylet 130. The optical fiber 135 is a multi-core optical fiber including a number of fiber Bragg gratings 136 disposed along a length of the optical fiber 135. The optical fiber 135 is configured to enable shape sensing of the optical fiber 135 based on reflected light signals emanating (i.e., reflected by) the fiber Bragg gratings 136. As the optical fiber 135 extends along the stylet 130, as the stylet 130 extends along the elongate body 125, and as the elongate body 125 is disposed within a lumen of the catheter, and the optical fiber 135 enables shape sensing of the catheter.

In some embodiments, the fiber Bragg gratings 136 may be configured to define light reflection signals based on conditions of the optical fiber 135, such as a temperature of the optical fiber 135, a motion of the optical fiber 135, or a displacement of fluid adjacent the optical fiber 135, such as via the Doppler effect, for example. Although not shown, in some embodiments, the optical fiber 135 may extend distally beyond the stylet distal end 130B.

In some embodiments, the optical fiber 135 may be configured to project illuminating light away from the stylet distal end 130B and receive imaging light entering the optical fiber 135 at the stylet distal end 130B. As such, the optical fiber 135 may obtain images of anatomical elements of the patient adjacent the stylet distal tip 130B during use.

In the illustrated embodiment, the optical fiber 135 extends away from the proximal portion 130C of the stylet 130 so that the optical fiber 135 may optically couple with the system module 110, such as via an optical connection member (not shown), for example. In some instances, the optical fiber 135 or optical connection member may extend through the sterile barrier 50.

The system module 110 is operatively coupled with the catheter placement device 120. More specifically, the system module 110 is (i) optically coupled with the optical fiber 135 and (ii) electrically coupled with the saline solution 140. In the illustrated embodiment, the system module 110 is configured to provide information pertaining to the placement of the catheter to the clinician such as displaying information and/or images (i.e., depicting images or information on the display 111). The system module 110 may include a console having a number of processors and logic stored in memory (e.g., a non-transitory computer-readable medium). The logic, when executed by the processors, governs the operation of the system module 110. The system module 110 further include a light source and an optical receiver.

The system module 110 is configured to (i) determine, based on reflected light signals emanating the fiber Bragg gratings 136, a shape 115 of the optical fiber 135, where the shape 115 represents the shape of the catheter, and (ii) display the shape 115, i.e., render an image of the shape 115 on the display 111. In some embodiments, the system module 110 may display the shape 115 in real time during advancement of the catheter along the vasculature to assist the clinician in placement of the catheter.

The system module 110 is configured to receive electrical signals from the catheter placement device 120, where in some instances, the electrical signals emanate from the patient, such as an electrocardiogram (ECG) signal, for example. In some embodiments, the system module 110 may a display an ECG waveform 116. In some instances, the ECG waveform 116 may vary in accordance with the location of the body distal tip 125B within the vasculature, such as within the superior vena cava, for example. In some embodiments, the logic may compare the ECG waveform 116 with an ECG waveform stored in memory, where the ECG waveform stored in memory is consistent with placement of the body distal end 125B within the lower one-third of the superior vena cava. As a result of the comparison, the logic may determine that the body distal end 125B is located within the lower one-third of the superior vena cava. Generally stated, the system module 110 may be configured to determine a placement location of the body distal end 125B (and, by association, the distal tip of the catheter) within a patient vasculature based on the electrocardiogram signal.

According to another embodiment, the proximal portion 130C of the stylet 130 may be electrically conductive defining an electrical path in leu of the wire 145 and the wire electrode 146. In such an embodiment, the optical fiber 135 and/or the optical connecting member may include an electrical conducting element 137 extending therealong. The electrical conducting element 137 may be electrically coupled with the proximal portion 130C and extend between the proximal portion 130C and system module 110. By way of summary, during use, the anatomy of the patient adjacent the body distal end 125B is electrically coupled with the system module 110 via the saline electrode 142, the saline solution 140 along the body lumen 124, the saline solution 140 within the compartment 126, the proximal portion 130C, and the electrical conducting element 137.

FIG. 2 is a distal end view of the elongate body 125 including an end view of the distal portion 130D of the stylet 130. To maximize cross-section area of the body lumen 124, the distal portion 130D may include an elongate opening 131 (i.e., a grove or slot) extending along the distal portion 130D. As such, the cross-sectional area of the elongate opening 131 adds to the annular cross-sectional area of the lumen 124.

Figure 3A:
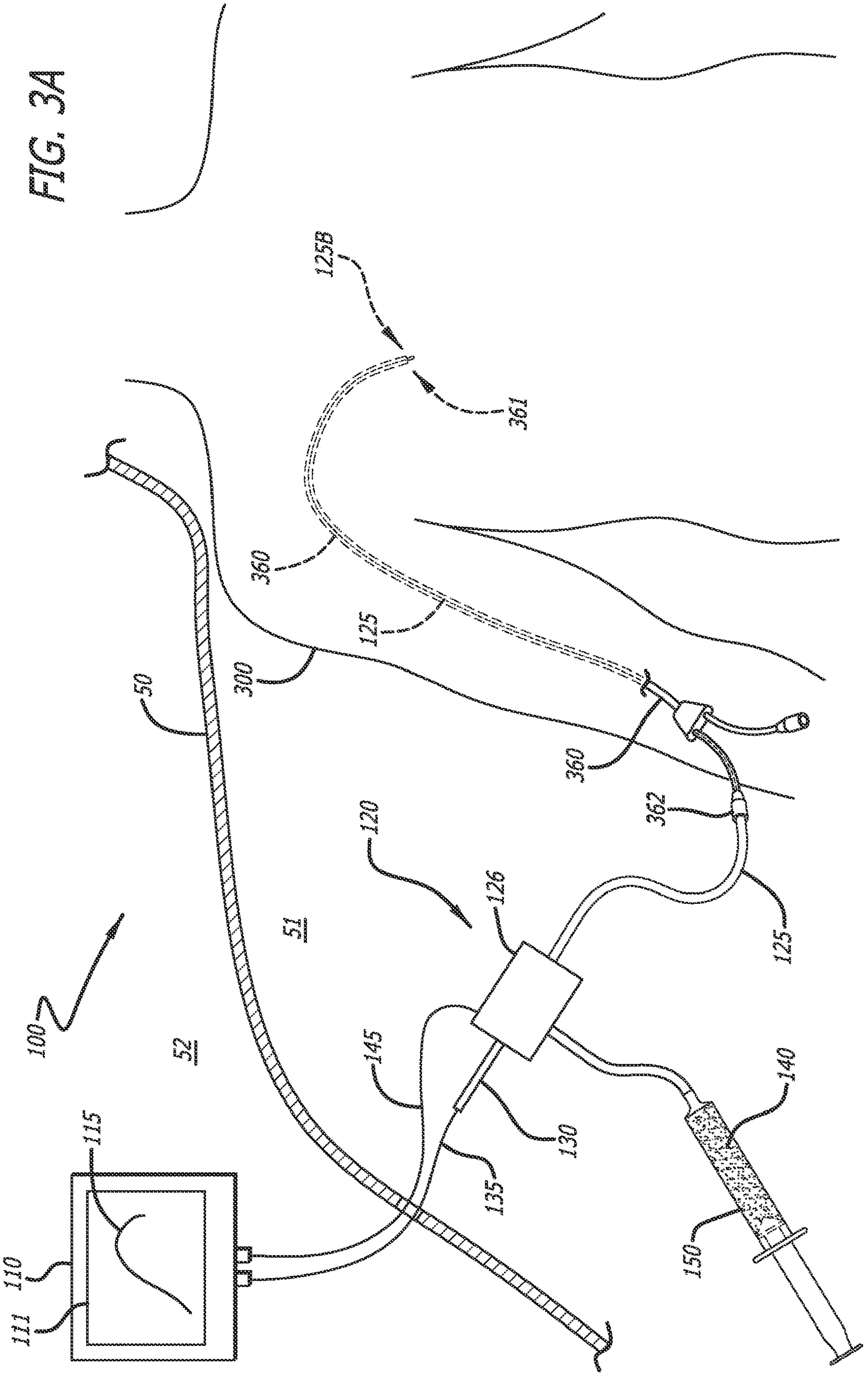
FIG. 3A illustrates the catheter placement system of FIG. 1 in use with a patient, in accordance with some embodiments.

FIG. 3A illustrates the system 100 in use with a patient 300. A catheter 360 (e.g., a PICC in the illustrated instance) is advanced along a vasculature of the patient 300. The elongate body 125 of the catheter placement device 120 is inserted into a lumen of the catheter 360 via a hub 362 of an extension leg of the catheter 360. The body distal end 125B is disposed adjacent a distal tip 361 of the catheter 360. The fluid delivery device 150 contains the saline solution 140 and the saline solution 140 is dispensed into the compartment 126 and along the lumen 124 (FIG. 1). The sterile barrier 50 is disposed between the system module 110 and the catheter placement device 120, where the optical fiber 135 and the wire 145 pass through the sterile barrier 50. The system module 110 renders an image of the shape 115 on the display 111.

Figure 3B:
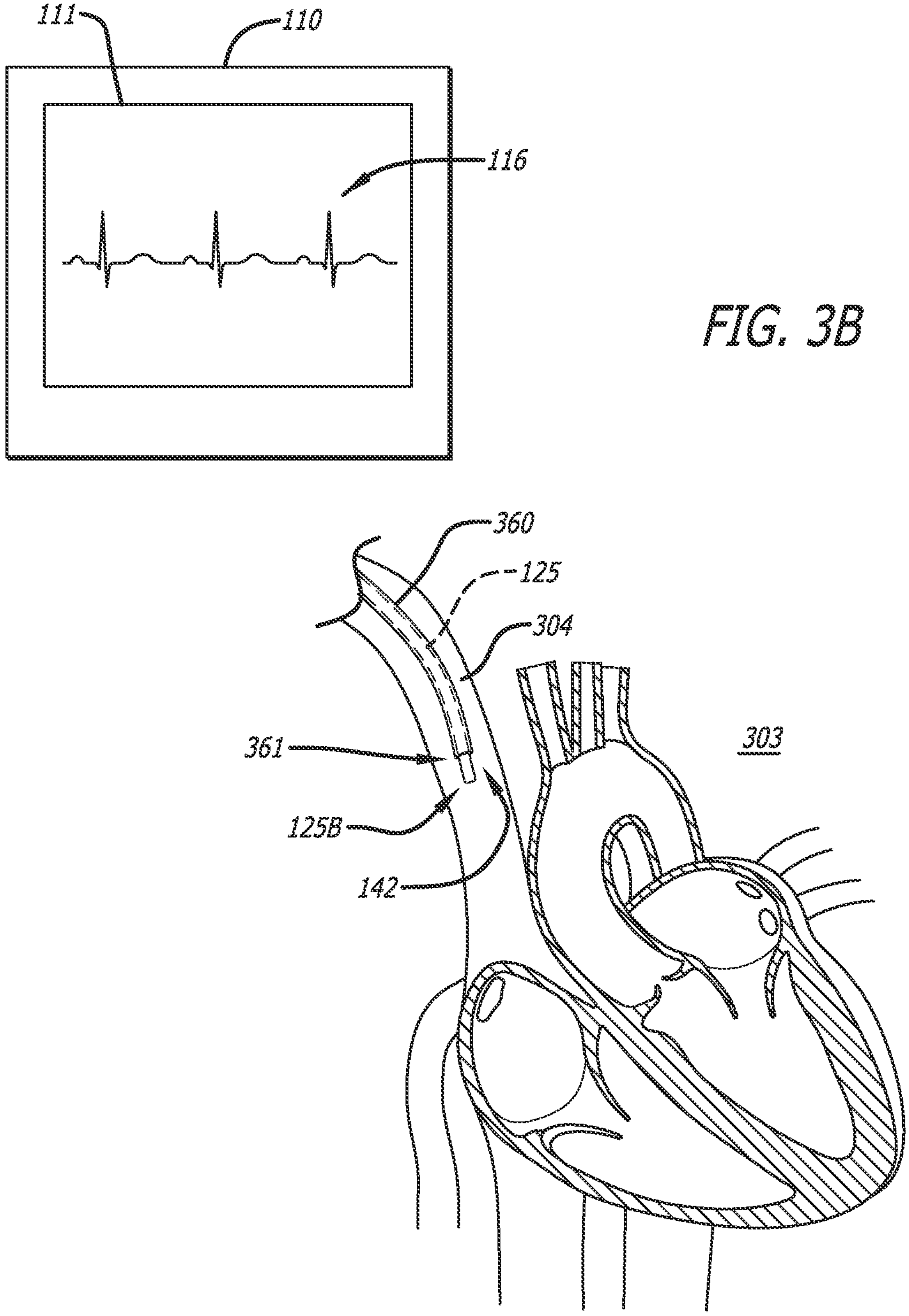
FIG. 3B illustrates a detailed view of a distal portion of the catheter placement device of FIG. 1 inserted within a superior vena cava of the patient, in accordance with some embodiments.

Referring now to FIG. 3B, a detailed view of distal portion of the elongate body 125, where the body distal end 125B and the distal tip 361 of the catheter 360 are disposed within the superior vena cava 304, is shown in accordance with some embodiments. The system module 110 including the display 111 is also shown. FIG. 3B illustrates a detailed perspective of the vasculature proximate to the heart 303 of a patient 300 as well as the anatomy of the heart 303. The saline electrode 142 is located with the superior vena cava 304 so as to obtain an ECG signal from the heart 303. The waveform 116 of the ECG signal is depicted on the display 111.

Figure 4:
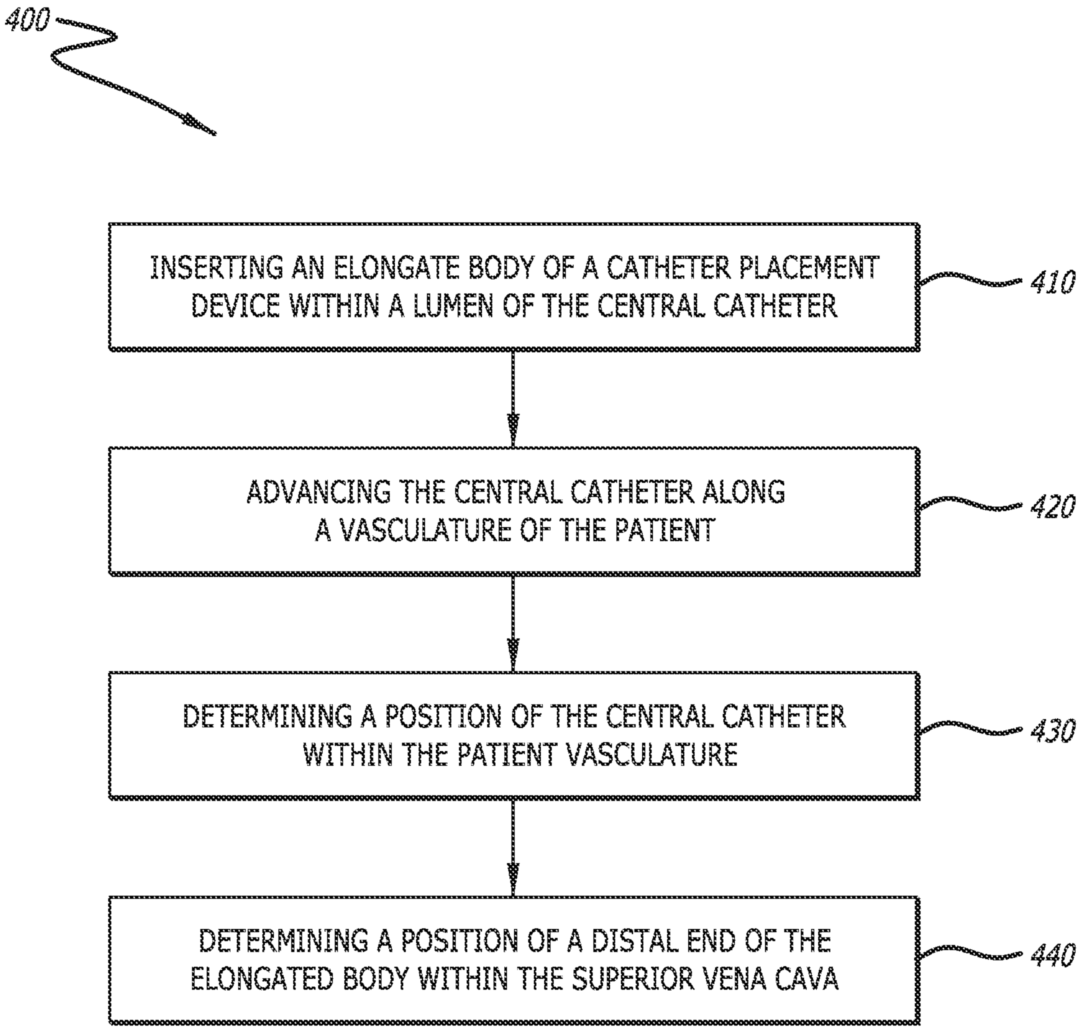
FIG. 4 illustrates a flow chart of an exemplary method for placing a catheter within a patient, in accordance with some embodiments.

FIG. 4 illustrates a flow chart of an exemplary method for placing a central catheter within a patient that may include all or any subset of the following steps, actions, or processes. The method 400 may include inserting an elongate body of the catheter placement device within the lumen of the central catheter (block 410). The catheter placement device is optically and electrically coupled with a catheter placement system module.

In accordance with the method 400, the catheter placement device includes the body lumen extending along the elongate body and the compartment coupled with the elongate body at a proximal end of the elongate body, where the compartment is in fluid communication with the body lumen. The saline solution is disposed within the compartment and the body lumen, such that the saline solution defines the electrical path along the elongate body. In some embodiments of the method 400, a syringe containing the saline solution is fluidly coupled with the compartment. In some embodiments of the method 400, the saline solution within the body lumen adjacent the distal end defines the electrode. In some embodiments of the method 400, the saline solution is electrically coupled with the system module via the wire, and the wire extends through a sterile barrier between a sterile environment and a non-sterile environment.

The stylet extends along the elongate body, where the stylet includes a multi-core optical fiber extending along the stylet, and where the multi-core optical fiber includes a number of fiber Bragg gratings disposed along a length of the multi-core optical fiber. In some embodiments of the method 400, the stylet is disposed with the body lumen.

The method 400 further includes advancing the central catheter along the vasculature of the patient (block 420). The method 400 may further include determining the position of the central catheter within the patient vasculature (block 430) based on a shape of the multi-core optical fiber, where the shape is determined by light reflection signals emanating from the fiber Bragg gratings. The method 400 may further include determining a position of the distal end of the elongate body within the superior vena cava (block 440) based on an electrocardiogram signal obtained from the patient via the saline electrode at the distal end.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter placement system, comprising:
a catheter placement device, comprising:
an elongate body configured for insertion into a catheter lumen, the elongate body including a body lumen extending between a body distal end and a body lumen opening at a body proximal end;
a compartment coupled with the elongate body at the body proximal end, the compartment fluidly coupled with the body lumen via the body lumen opening;
a saline solution disposed within the compartment and the body lumen; and
a stylet extending along the elongate body and through the body lumen opening, the stylet including a multi-core optical fiber extending along the stylet, the multi-core optical fiber including a number of fiber Bragg gratings disposed along a length of the multi-core optical fiber.

2. The system according to claim 1, wherein a distal portion of the stylet is disposed within the body lumen.

3. The system according to claim 2, wherein the stylet includes an elongate opening extending along the distal portion, the elongate opening defining an additional cross-sectional area of the body lumen.

4. The system according to claim 1, wherein the catheter placement device is optically coupled with a system module.

5. The system according to claim 4, wherein the system module is configured to determine a shape of the stylet based on reflected light signals emanating the fiber Bragg gratings.

6. The system according to claim 5, wherein the system module is configured to display the shape.

7. The system according to claim 4, wherein the system module is further configured to display an image acquired by the multi-core optical fiber.

8. The system according to claim 4, wherein the system module is further configured to determine, based on reflected light signals emanating the fiber Bragg gratings, one or more of:
a temperature of the multi-core optical fiber,
a motion of the multi-core optical fiber, or
a displacement of fluid adjacent the multi-core optical fiber.

9. The system according to claim 4, wherein the saline solution is electrically coupled with the system module and a patient.

10. The system according to claim 9, wherein the saline solution is electrically coupled with the system module via a wire.

11. The system according to claim 10, wherein the wire extends through a sterile barrier between a sterile environment and a non-sterile environment.

12. The system according to claim 9, wherein the system module is configured to determine an electrocardiogram signal of the patient and display an electrocardiogram waveform.

13. The system according to claim 12, wherein the system module is configured to determine a placement location of the body distal end within a vasculature of the patient based on the electrocardiogram signal.

14. The system according to claim 1, wherein:
the stylet extends through the compartment, and
a proximal portion of the stylet extends proximally away from the compartment.

15. The system according to claim 14, wherein the proximal portion of the stylet is:
electrically conductive,
electrically coupled with the saline solution within the compartment, and
electrically coupled with a system module.

16. The system according to claim 1, wherein the catheter placement device further comprises a fluid delivery device containing the saline solution, the fluid delivery device fluidly coupled with the compartment.

17. The system according to claim 16, wherein:
the compartment includes a side port, and
the fluid delivery device is fluidly coupled with the compartment via the side port.

* * * * *